United States Patent [19]

Binder

[11] Patent Number: 4,499,286
[45] Date of Patent: Feb. 12, 1985

[54] DERIVATIVES OF THIENYLACETIC ACID AMIDES AND THEIR PHARMACEUTICALLY ACCEPTABLE ACID SALTS AND A PROCESS FOR THE PREPARATION THEREOF

[75] Inventor: Dieter Binder, Vienna, Austria

[73] Assignee: Leavoson-Gesellschaft m.b.H. & Co. KG, Linz, Austria

[21] Appl. No.: 554,416

[22] Filed: Nov. 22, 1983

[30] Foreign Application Priority Data

Nov. 26, 1982 [AT] Austria ............... 4308/82

[51] Int. Cl.³ ............... C07C 103/82; A61K 31/38
[52] U.S. Cl. ............... 548/527; 546/213; 549/76
[58] Field of Search ............ 549/76; 548/527; 546/213

[56] References Cited

U.S. PATENT DOCUMENTS 4,098,904 7/1978 Szmuszkovicz ............ 549/76
4,192,885 3/1980 Szmuszkovicz ............ 549/76

Primary Examiner—Alan Siegel
Attorney, Agent, or Firm—Sughrue, Mion, Zinn, Macpeak & Seas

[57] ABSTRACT

Novel derivatives of thienylacetic acid amides of the general formula

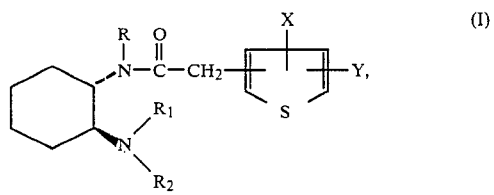

in which the two nitrogens on the cyclohexane ring are transconnected, the basic acetic acid amide radical is in position 2 or 3 of the thiophene nucleus, R is $C_1$–$C_3$ alkyl, $R_1$ and $R_2$ are independently $C_1$–$C_3$-alkyl or represent together with the nitrogen atom to which they are attached a pyrrolidine or piperidine ring and X and Y are independently hydrogen, chlorine or bromine in position 2 to 5 of the thiophene nucleus in dependence on the position of the basic acetic acid amide group, and their pharmaceutically acceptable acid addition salts are $\mu$-specific analgetics, which do not cause any physical dependence. Therefore, they are suitable for protracted treatment of pain conditions.

4 Claims, No Drawings

DERIVATIVES OF THIENYLACETIC ACID AMIDES AND THEIR PHARMACEUTICALLY ACCEPTABLE ACID SALTS AND A PROCESS FOR THE PREPARATION THEREOF

SUMMARY OF THE INVENTION

The present invention relates to novel therapeutically useful derivatives of thienylacetic acid amides of the general formula

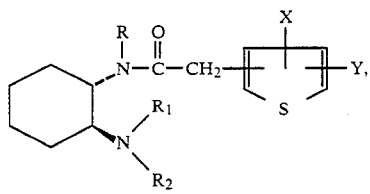

in which the two nitrogens on the cyclohexane ring are transconnected, the basic acetic acid amide radical is in position 2 or 3 of the thiophene nucleus, R is $C_1$–$C_3$ alkyl, $R_1$ and $R_2$ are independently $C_1$–$C_3$-alkyl or represent together with the nitrogen atom to which they are attached a pyrrolidine or piperidine ring and X and Y are independently hydrogen, chlorine or bromine in position 2 to 5 of the thiophene nucleus in dependence on the position of the basic acetic acid amide group, and their pharmaceutically acceptable acid addition salts as well as to a process for the preparation thereof.

The novel compounds of general formula (I) show high analgetic properties in different animal models without causing any physical dependence (addiction). Therefore, they are excellently suitable for protracted treatment of different pains.

The process of the invention is characterized in that a compound of the general formula

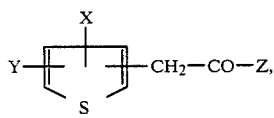

in which the acetic acid halide radical is in Position 2 or 3 of the thiophene nucleus, X and Y are as defined above and Z is chlorine or bromine, is reacted with a trans-cyclohexane-1,2-diamine of the general formula

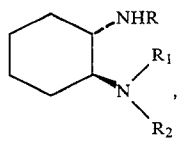

in which R, $R_1$ and $R_2$ are as defined above.

DETAILED DESCRIPTION OF THE INVENTION

The formation of the acid amide is carried out usually in an inert solvent such as e.g. chloroform, methylene chloride, ether or dioxane. It is most convenient to introduce the amines of formula (III), preferably together with at least equimolar amounts of a highly volatile, strongly basic acid acceptor, such as e.g. triethylamine, and to drop thereto the acid chlorides of formula (II), diluted with the used solvent, in equivalent amounts, preferably in a slight excess, at temperatures of about 20° C. The reaction is completed in 18 hours at the latest at this temperature.

For working up the reaction solution is shaken with saturated solution of sodium bicarbonate, the organic phase is separated, dried and evaporated. By extracting the residue with boiling ether and filtration over activated charcoal the crude oily base of formula (I) is obtained which for further purification may be subjected to column chromatography (e.g. Kieselgel 60 Merck, article 7734; eluent: benzene/triethylamine 9:1) or converted into crystalline pharmaceutically acceptable acid addition salts, e.g. hydrochlorides. The latter may be purified by recrystallization.

For that purpose the crude base of formula (I) is dissolved in a suitable solvent, e.g. a lower alkanol or water, an equivalent protonic acid is added, the solvent is evaporated in vacuo and the residue is crystallized from methanol, optionally with addition of ether, or the crude free base of formula (I) is dissolved in ether or benzene, the acid addition salts are precipitated by addition of the corresponding protonic acid and recrystallized, as described above. Suitable examples of such pharmaceutically acceptable salts in addition to the salt of the hydrochloric acid are the salts of sulphuric acid, nitric acid, phosphoric acid, sulfonic acids, benzoic acid, succinic acid, maleic acid, tartaric acid and citric acid.

The acid addition salts of the invention possess the same high analgetic activity such as the corresponding free bases of compound (I).

The compounds of formula (III) are known from the literature. As far as they are not known from the literature the thienylacetic acid halides of formula (II) may be obtained from the corresponding thienylacetic acids (formula X) in a manner known to the man skilled in the art, e.g. by heating in an excess of thionyl chloride or bromide.

As far as the thienylacetic acids are not known from the literature they may be prepared starting from thiophene carboxylic acids of formula (IV) known from the literature by the following synthesis familiar to the man skilled in the art:

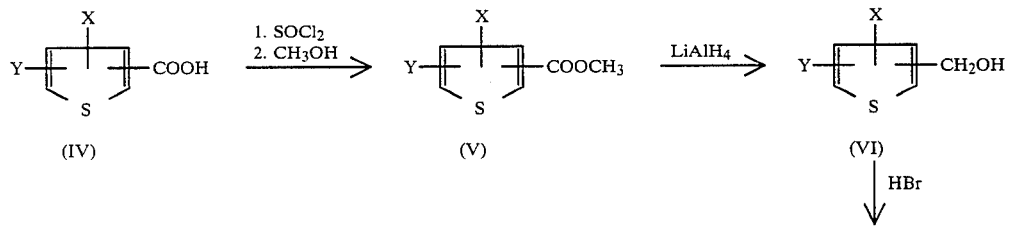

-continued

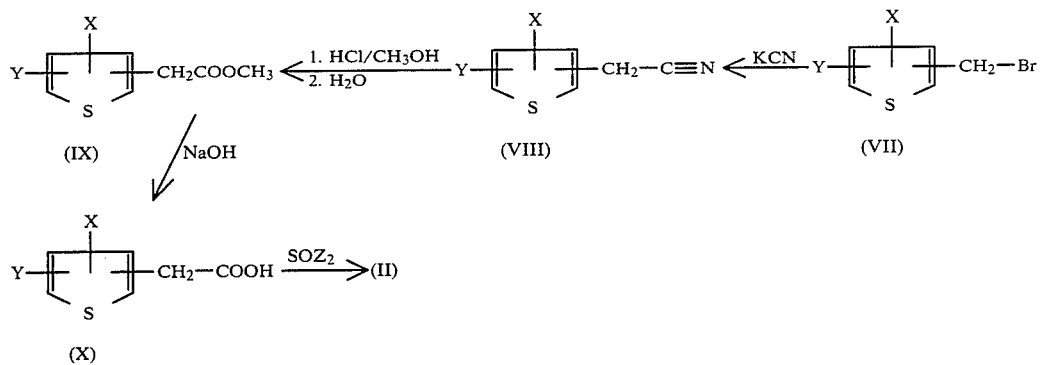

in which X, Y and Z are as defined above.

The following example illustrates the invention without limiting it thereto.

EXAMPLE trans-N-Methyl-N-[2-(1-pyrrolidinyl)-cyclohexyl]-4,5-dichloro-2-thienylacetic acid amide hydrochloride (formula I; R=CH₃,

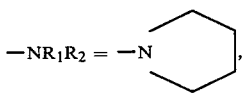

X=4-Cl, Y=5-Cl) [LG -83-8-01]

A solution of 1,61 g (7,01 mmoles) of 4,5-dichloro-2-thienylacetic acid chloride (formula (II); X=4-Cl, Y=5-Cl, Z=Cl) in 15 ml of absolute chloroform is dropped to a solution of 1,24 g (6,80 mmoles) of trans-N-methyl-2-(1-pyrrolidinyl)cyclohexylamine (formula III; R=methyl,

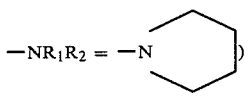

and 0,69 g (6,80 mmoles) of triethylamine in 60 ml of absolute chloroform for 15 minutes at room temperature and then stirred 18 hours at room temperature. Thereafter the reaction solution is shaken out with saturated solution of sodium hydrogen carbonate, the organic phase is washed with water, dried over sodium sulfate and evaporated. The oily residue consisting of the crude base of formula (I) and some ether-insoluble by-product is taken up with 30 ml of ether, filtered over activated charcoal and HCl-gas is introduced into the solution. The precipitated crystalline hydrochloride is sucked off, dissolved in 4 ml of methanol, precipitated with 50 ml of wet ether, sucked off and the operation is repeated once. The colorless crystals are dried at 13,3 Pa and room temperature for 5 hours. Thus the non-hygroscopic hemihydrate of the hydrochloride is obtained. Yield 57%. M.p. 216°–218° C. The compound free of crystal water obtained by drying in vacuo at 13,3 Pa and 140° C. is hygroscopic.

In analogous manner there are obtained:
trans-N-methyl-N-[2-(1-pyrrolidinyl)-cyclohexyl]-5-chloro-2-thienylacetic acid amide hydrochloride (formula I; R=CH₃,

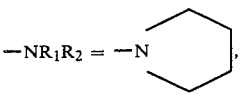

X=H, Y=5-Cl), m.p. (methanol/ether): 175°–178° C. (60%), compound free of crystal water, colorless crystals, non-hygroscopic.

trans-N-methyl-N-[2-(1-pyrrolidinyl)-cyclohexyl]-2,5-dichloro-3-thienylacetic acid amide hydrochloride (formula I; R=CH₃,

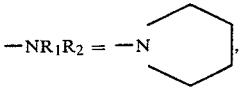

X=2-Cl, Y=5-Cl), [LG-83-8-02], m.p. (methanol/ether): 252°–254° C. (55%), compound free of crystal water, colorless crystals, non-hygroscopic.

The starting material may be obtained as follows:
4,5-dichloro-2-thienylacetic acid chloride (formula II;

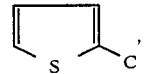

X=Cl, Y=5-Cl, Z=Cl)

1,48 g (7,01 mmoles) of 4,5-dichloro-2-thienylacetic acid are dissolved in 15 ml of thionyl chloride and heated under reflux for 2 hours. Then the excess of thionyl chloride is distilled off in vacuo and the remaining acid chloride is used without further purification in the next step. Crude yield: almost quantitative.

In analogous manner there are prepared: 5-chloro-2-thienylacetic acid chloride and 2,5-dichloro-3-thienylacetic acid chloride.

The pharmacological study of two compounds of the invention, namely LG 83-8-01 and LG 83-8-02, showed that the compounds of the invention are μ-specific analgetics.

Both compounds showed in the tail-flick analgesy test on the mouse a ED₅₀ of 0,48 mg/kg body weight at a LD₅₀ of about 50 mg/kg, and the typical μ-receptor agonistic properties, as they occur with the opiates, namely the Straub tail phenomen, the arched back and an increased locomotive activity, could not be observed.

The compounds of the invention can be used in form of tablets or capsules containing a dose unit of the compounds together with diluents such as corn starch, calcium carbonate, dicalcium phosphate, alginic acid, lactose, magnesium stearate, Primogel (trade mark) or talcum for oral application. Tablets are prepared in conventional manner by granulating and compressing the ingredients, capsules are prepared by filling the ingredients into hard gelatine capsules of suitable size.

The compounds of the invention can be administered also parenterally, e.g. by intramuscular, intravenous or subcutaneous injection. For parenteral application it is most convenient to use the compounds in form of a sterile aqueous solution which may contain other dissolved substances such as tonic substances and substances for adjusting the pH-value. The compounds can be added to distilled water and the pH-value can be adjusted by using an acid such as citric acid, lactic acid or hydrochloric acid to 3 to 6. Sufficient solutes such as dextrose or saline solution may be added so as to make the solution isotonic. The obtained solution can be sterilized and filled into sterile glass ampoules of suitable size, so that they contain the desired volume of the solution. The compounds of the invention may be administered also by infusion of a parenteral formulation as described above into a vein. For oral administration to human beings it is supposed that the daily dosage of a compound of the invention is in the range of from 0,1 to 10 mg/kg per day for a typical adult person weighing 70 kg.

However, in each case the physician will determine the real dosage most suitable for the patient, which dosage may vary in accordance with the age, the weight and the reaction of the patient.

What is claimed is:

1. A thienylacetic acid amide of the general formula

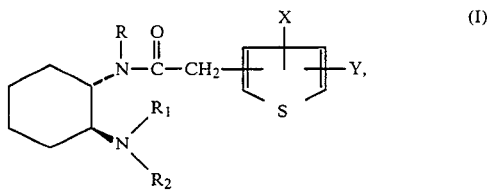

in which the two nitrogens on the cyclohexane ring are transconnected, the basic acetic acid amide radical is in position 2 or 3 of the thiophene nucleus, R is $C_1$-$C_3$ alkyl, $R_1$ and $R_2$ are independently $C_1$-$C_3$-alkyl or represent together with the nitrogen atom to which they are attached a pyrrolidine or piperidine ring and X and Y are independently hydrogen, chlorine or bromine in position 2 to 5 of the thiophene nucleus in dependence on the position of the basic acetic acid amide group, and their pharmaceutically acceptable acid addition salts.

2. trans-N-Methyl-[2-(1-pyrrolidinyl)-cyclohexyl]-4,5-dichloro-2-thienylacetic acid amide.

3. trans-N-Methyl-N-[2-(1-pyrrolidinyl)-cyclohexyl]-5-chloro-2-thienylacetic acid amide.

4. trans-N-Methyl-N-[2-(1-pyrrolidinyl)-cyclohexyl]-2,5-dichloro-3-thienylacetic acid amide.

* * * * *